United States Patent [19]

Lukevits et al.

[11] Patent Number: 4,841,054
[45] Date of Patent: Jun. 20, 1989

[54] 2,6-DIMETHYL-3,5-DIMETHOXYCARBO-NYL-4-(5'-TRIMETHYLSILYL-2'-FURYL)-1,4-DIHYDROPYRIDINE

[76] Inventors: Edmund Y. Lukevits, ulitsa Ierikju,43,kv.10; Valeria V. Kastron, ulitsa Avotu,33,kv.2; Rasma O. Vitolin, ulitsa Suvorova,117,kv.13; Nikolai P. Erchak, ulitsa Dzirnavu,161,kv.13; Indulis P. Skrastinsh, ulitsa Lienes,9,kv.26; Gunar Y. Dubur, ulitsa Ierikju,43,kv.2; Agris A. Kimenis, ulitsa Staitseles,15,kv.208, all of Riga, U.S.S.R.

[21] Appl. No.: 239,953

[22] PCT Filed: Oct. 21, 1986

[86] PCT No.: PCT/SU86/00104
 § 371 Date: May 26, 1988
 § 102(e) Date: May 26, 1988

[87] PCT Pub. No.: WO88/03143
 PCT Pub. Date: May 5, 1988

[51] Int. Cl.$^4$ .............................................. C07F 7/10
[52] U.S. Cl. ...................................................... 546/14
[58] Field of Search ................... 546/14, 283; 514/63, 514/336

[56] References Cited

U.S. PATENT DOCUMENTS 4,237,137 12/1980 Tacke et al. .............................. 546/14
4,277,483 7/1981 Materne et al. ......................... 546/14

FOREIGN PATENT DOCUMENTS 2837477 3/1980 Fed. Rep. of Germany .
2915355 10/1980 Fed. Rep. of Germany .
 542884 11/1973 Switzerland .
 626375 11/1981 Switzerland .

OTHER PUBLICATIONS

E. Kusano, et al., Arzheim.–Forsch, 32, "Hypotensive Effect of Nifedipine in Hypertensive Patients with Chronic Renal Failure", 1575–1580, (1982).
R. Tacke, et al., Eur. J. of Med. Chem., 18, "Sila-Analgaes of Nifedipine-like . . . ", 155–161 (1983).
V. Kastron, et al., Khimiko–Pharmaceticheskij Zhournal, No. 6, "Synthesis and Pharmacological Activity of . . . ", 57–62 (1979).

Primary Examiner—Glennon H. Hollrah
Assistant Examiner—Mark W. Russell
Attorney, Agent, or Firm—Burgess, Ryan & Wayne

[57] ABSTRACT

2,6-dimethyl-3,5-dimethoxycarbonyl-4-(5'-trimethylsilyl-2'-furyl)-1,4-dihydropyridine which has the formula

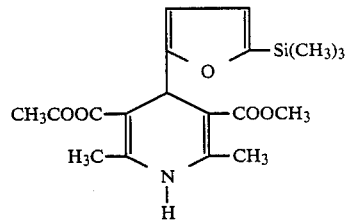

This compound exhibits a hypotensive activity.

1 Claim, No Drawings

2,6-DIMETHYL-3,5-DIMETHOXYCARBONYL-4-(5'-TRIMETHYLSILYL-2'-FURYL)-1,4-DIHYDROPYRIDINE

FIELD OF THE INVENTION

The present invention relates to the art of organic synthesis, more specifically, to 1,4-dihydropyridine derivatives and, more particularly, to 2,6-dimethyl-3,5-dimethoxycarbonyl-4-(5'-trimethylsilyl-2'-furyl)-1,4-dihydropyridine.

The above-mentioned 1,4-dihydropyridine derivatives have hypotensive and coronarodilating effects and some of them are useful in medicine.

PRIOR ART

The most widespread 1,4-dihydropyridine derivatives is 2,6-dimethyl-3,5-dimethoxycarbonyl-4-(O-nitrophenyl)-1,4-dihydropyridine (Nifedipine) possessing hypotensive and coronarodilating effects (Arzneium.-Forsch, V.32, 1982, E. Kusano, J. Asano, K. Takeda, J. Matsumoto, A. Ebihar. "Hypotensive Effect of Nifedipine in Hypertensive Patients with Chronic Renal Failure", pp. 1575–1580).

Though Nifedipine is widely used in the medical practice, it is unstable in light and highly toxic.

The known 1,4-dihydropyridine derivatives containing silicon in the 3,5-ester group are substantially inferior to Nifedipine as regards their hypotensive activity (Eur. J. Med. Chem., V.18, No.2, 1983, R. Tacke, A. Bentlage, R. Towart, E. Möller, "Sila-Analogues of Nifediphine-Like dialkyl 2,6-dimethyl-4-aryl-1,4-dihydropyridine-3,5-dicarboxylates", pp. 155–161).

Among 1,4-dihydropyridine derivatives known in the art is 2,6-dimethyl-3,5-dimethoxycarbonyl-4-(2'-furyl)-1,4-dihydropyridine which also displays a hypotensive activity, though considerably lower than that of Nifedipine (Khimiko-pharmaceuticheskij Zhournal, No.6, 1979, V. V. Kastron, G. Ya. Dubur, R. O. Vitolin', A. A. Kimenis "Synthesis and pharmacological activity of 4-furyl-1,4-dihydropyridines", pp.57–62).

The above-mentioned derivatives of 1,4-dihydropyridine, though possess a hypotensive effect, this effect is not lasting which necessitates their repeated administration during the day's period. Furthermore, Nifedipine has a high toxicity.

DISCLOSURE OF THE INVENTION

The present invention is directed to the provision of such a derivative of 1,4-dihydropyridine which would exhibit a protracted hypotensive effect and, at the same time, would have a low toxicity.

This object is accomplished by a derivative of 1,4-dihydropyridine which, according to the present invention, is 2,6-dimethyl-3,5-dimethoxycarbonyl-4-(5'-trimethylsilyl-2'-furyl)-1,4-dihydropyridine of the formula

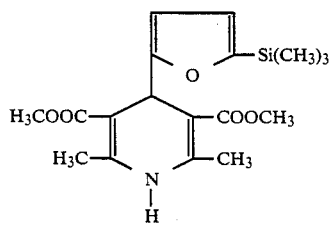

This compound is novel. We have found that this compound displays a protracted hypotensive effect and has a relatively low toxicity.

This compound comprises a crystalline substance of a yellowish shade and m.p. of 158°–159° C. It is well soluble in methanol, ethanol, chloroform, acetone and substantially insoluble in water. This compound is stable both in the crystalline state and as solutions. When solid, upon storage in the light this compound does not change its UV spectrum within a year's period. In a alcoholic solution of the concentration of $5 \times 10^{-5}$ mol the UV spectrum remained unchanged for 6 months. At the same time, in the UV spectrum of Nifedipine under similar conditions a maximum of the oxidized form of Nifedipine is observed already within 6 hours.

This compound is prepared by the method comprising condensation of methyl ester of acetoacetic acid, ammonia and 5-trimethylsilylfurfurol in solution of methanol. Furthermore, this compound can be obtained by condensation of methyl ester of acetoacetic acid, methyl ester of β-aminocrotonic acid and 5-trimethylsilylfurfurol in a medium of an organic solvent. The reaction is carried out under normal pressure under heating. The product is obtained in a good yield.

The starting components employed for the preparation of the above-mentioned compound are known and available substances.

The pharmacological study of the compound according to the present invention was conducted in comparison with a preparation of the same series employed in clinical practice, viz. Nifedipine.

In experiments on spontaneously hypertensive rats the compound according to the present invention upon a single administration (10 mg/kg in stomach) caused reduction of systolic arterial pressure. The maximum hypotensive effect (by 21 %) was observed by the 6-th hour after administration of the compound, after 24 hours the pressure was reduced by 17 % as compared to the initial value. A single-time administration of the compound for 5 days in the dose of 10 mg/kg into the stomach caused the maximum reduction of the pressure (by 22 %) on the 6-th day, i.e., one day after discontinuation of administration of the compound. A reduced pressure was observed on the 3-rd day (by 10 %) after discontinuation of the administration. In comparison with Nifedipine it was clear that the latter was superior to the compound of the present invention by the 1-st hour after administration, by the 6-th hour both compounds showed the same hypotensive effect and 24 hours after the administration the compound of the present invention still produced the hypotensive effect, whereas in the rats administered with Nifedipine the systolic pressure returned to the initial level. Therefore, the compound according to the present invention is superior over Nifedipine as regards the duration of its effect upon a single and repeated administration and it provides a less pronounced effect on the heart rate. The data of the studies are shown in Table 1 hereinbelow. For the purpose of comparison this Table also shows the data for 2,6-dimethyl-3,5-dimethoxycarbonyl-4-(2'-furyl)-1,4-dihydropyridine which is an analog of the compound according to the present invention as regards its chemical structure.

TABLE 1

Effect of compounds on arterial pressure in experiments on spontaneously hypertensive rats

| Compound | Dose, mg/kg | Hypotensive effect, %, after | | | |
|---|---|---|---|---|---|
| | | 1 hr | 6 hrs | 24 hrs | 48 hrs |
| Of this invention | 10 | 13 | 21 | 17 | — |
| | 20 | — | 30 | 39 | 28 |
| Analog | 10 | 12 | 7 | 0 | 0 |
| Nifedipine | 10 | 34 | 23 | 0 | 0 |

As it is seen from Table 1, the compound according to the present invention has a more lasting hypotensive effect than the analog and Nifedipine.

We have found that this compound in the doses of 10 and 20 mg/kg in experiments on spontaneously hypertensive rats (SHR) upon a peroral administration either lowers the heart rate or does not change it. As regards this effect, the compound according to the present invention is positively distinguished from Nifedipine causing tachycardia.

The acute toxicity of the compound according to the present invention, that of Nifedipine and the analog was studied on white nondescript mice upon an intraperitoneal administration. The mice were observed for 10 days. The mean lethal dose ($LD_{50}$) was determined by the Litchfield and Wilcoxon method. The administration of the compound according to the present invention in doses of up to 1,000 mg/kg did not cause death of the mice. The data on the study of the acute toxicity are shown in Table 2 hereinbelow.

TABLE 2

| Compound | Acute toxicity $LD_{50}$, mg/kg |
|---|---|
| Of the present invention | above 1,000 |
| Analog | 2,900 |
| Nifedipine | 185 (119–287) |

It is seen from Table 2 hereinabove that the compound according to the present invention has a low toxicity as compared to Nifedipine. Though the analog has a low toxicity as well, its hypotensive properties are subtantially lower than those of the compound of the present invention.

Taking into consideration a clearly pronouced and protracted hypotensive effect of the compound of the present invention, as well as its low toxicity and a high stability as compared to the prior art preparation Nifedipine, it can be recommended for the treatment of hypertensive disease. The duration of the effect produced by the compound according to the present invention makes it possible to assume that the therapeutic effect can be attained by a single-time adiministration of the compound a day.

BEST MODE FOR CARRYING OUT THE INVENTION

The above-identified compound, viz. 2,6-dimethyl-3,5-dimethoxycarbonyl-4-(5'-trimethylsilyl-2'-furyl)-1,4-dihydropyridine should be prepared by the method comprising condensation of methyl ester of acetoacetic acid, methyl ester of β-aminocrotonic acid and 5-trimethylsilylfurfurol in the emdium of methanol. The reaction is carried out at the temperature of boiling of the reaction mixture under normal pressure. The completion of the reaction is determined by the thin-layer chromatography method. On completion of the reaction the reaction mixture is cooled and the resulting precipitate of the desired product is separated. The yield of the product after crystallization is 61.7 %. The product thus obtained corresponds to the above-given formula.

For a better understanding of the present invention, an example illustrating preparation of the compound according to this invention is given hereinbelow.

EXAMPLE 2.45 g (1.45 mmol) of 5-trimethylsilylfurfurol, 1.68 g (1.45 mmol) of acetoacetic acid methyl ester and 1.66 g (1.45 mmol) of β-aminocrotonic acid methyl ester are boiled for 3 hrs in 10 ml of methanol. A yellow precipitate is formed upon cooling. The precipitate is washed with hexane to give 4.5 g (92.5 %) of the compound. After recrystallization from methanol 3 g (61.7 %) of the product are obtained. M.p. 158°–159° C. $R_f$ 0.70 (hexane-chloroform-ethylacetate, 1:1:1). UV spectrum, $\lambda_{max}$, nm (1g): 234 (4.46), 352 (3.92). IR spectrum, $cm^{-1}$: 1,659; 1,715; 3,365. PMR spectrum, δ, ppm: (4-H); 5.64 g (3'-H, furan). J=2 Hz; 6.45 d (4'-Hλ, furan). J=2 Hz.

Found, %: C 59.17: H 6.41; N 3.84. $C_{18}H_{25}NO_5Si$. Calculated, %: C 59.48; H 6.93; N 3.85.

INDUSTRIAL APPLICABILITY

The composition according to the present invention, viz. 2,6-dimethyl-3,5-dimethoxycarbonyl-4-(5'-trimethylsilyl-2'-furyl)-1,4-dihydropyridine can be useful in the pharmaceutical industry for the manufacture of a medicated preparation intended for the treatment of the hypertensive disease.

We claim:

1. 2,6-dimethyl-3,5-dimethoxycarbonyl-4-(5'-trimethylsilyl-2'-furyl)-1,4-dihydropyridine of the formula:

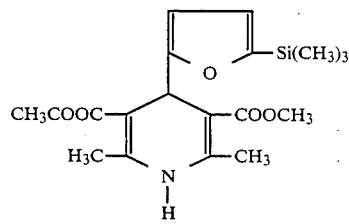

* * * * *